United States Patent [19]

Anand et al.

[11] Patent Number: 5,221,669

[45] Date of Patent: Jun. 22, 1993

[54] ANTIVIRAL COMPOSITIONS CONTAINING ALPHA-CYCLODEXTRIN SULFATES ALONE AND IN COMBINATION WITH OTHER KNOWN ANTIVIRAL AGENTS AND GLUCOCORTICOIDS AND METHODS OF TREATING VIRAL INFECTIONS

[75] Inventors: Rita Anand, Rockville; Joseph Pitha, Baltimore, both of Md.

[73] Assignee: The United States of America as represented by the Department of Health and Human Services, Washington, D.C.

[21] Appl. No.: 687,599

[22] Filed: Apr. 19, 1991

[51] Int. Cl.[5] .................. A61K 31/715; A61K 31/70; A61K 31/56

[52] U.S. Cl. ..................... 514/58; 514/50; 514/169; 514/934

[58] Field of Search .................. 514/58, 50, 169, 934

[56] References Cited

U.S. PATENT DOCUMENTS

| | | | |
|---|---|---|---|
| 4,020,160 | 4/1977 | Bernstein et al. | 514/58 |
| 4,247,535 | 1/1981 | Lewis et al. | 514/58 |
| 4,258,034 | 3/1981 | Joseph et al. | 536/18.2 |
| 4,818,538 | 4/1989 | Rideout et al. | 424/436 |
| 4,956,351 | 9/1990 | Mesens et al. | 514/58 |
| 5,024,998 | 6/1991 | Bodor | 514/58 |

FOREIGN PATENT DOCUMENTS 2090738 7/1982 United Kingdom ................ 514/58

OTHER PUBLICATIONS

Goodman & Gilman, *The Pharmacological Basis of Therapeutics*, Sixth Edition, pp. 1273.

Schols et al, (1991) *Chemistry & Chemotherapy*, 2(1), pp. 45–53.

*Primary Examiner*—John W. Rollins
*Attorney, Agent, or Firm*—Birch, Stewart, Kolasch & Birch

[57] ABSTRACT

The present invention is directed to antiviral compositions containing $\alpha$-cyclodextrin sulfates alone and in combination with other known antiviral agents and glucocorticoids and methods of treating viral infections.

13 Claims, 1 Drawing Sheet

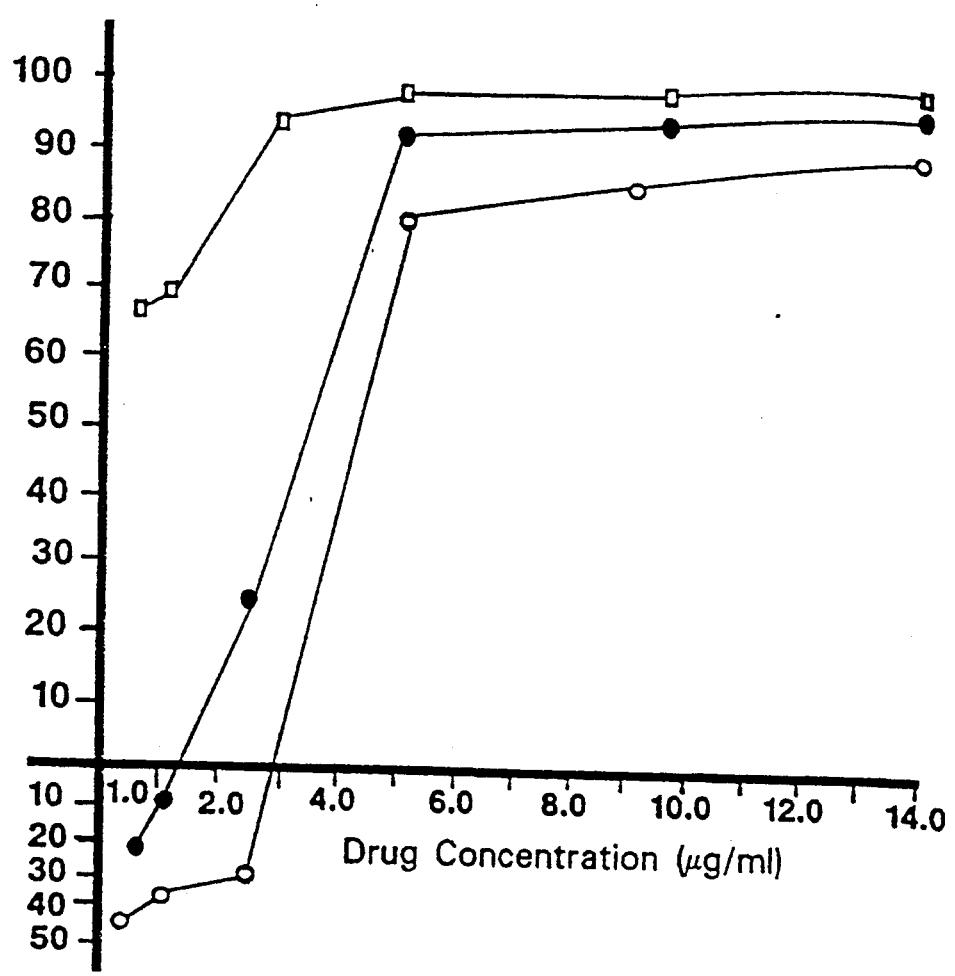

ANTIVIRAL COMPOSITIONS CONTAINING ALPHA-CYCLODEXTRIN SULFATES ALONE AND IN COMBINATION WITH OTHER KNOWN ANTIVIRAL AGENTS AND GLUCOCORTICOIDS AND METHODS OF TREATING VIRAL INFECTIONS

BACKGROUND OF THE INVENTION

Acquired immune deficiency syndrome (AIDS) is characterized by immunosuppression which predisposes patients to opportunistic infections and certain unusual forms of neoplasms. This syndrome was first recognized as a clinical entity in 1981 (Gottlieb et al., (1981) Pneumocystis carinii pneumonia and mucosal candidiasis in previously healthy homosexual men: evidence of new acquired cellular immunodeficiency. New Engl J Med 305:1425-1431; Masur et al., (1981) An outbreak of community-acquired pneumocystic carinii pneumoniae: initial manifestation of cellular immune dysfunction. New Engl J Med 305:1431-1438; Siegal et al., (1981) Severe acquired immunodeficiency in male homosexuals, manifested by chronic perional ulcerative herpes simplex lesion. New Engl J Med 305:1439-1444). In 1984, a human retrovirus, HIV-1, was found to be the cause of AIDS (Barre-Sinoussi et al., (1983) Isolation of a Tlymphotropic retrovirus from a patient at risk for acquired immune deficiency syndrome. Science 220:868-871; Gallo et al., (1984) Frequent detection and isolation of cytopathic retroviruses (HTLV-III) from patients with AIDS and pre AIDS. Science 224:500-503; popovic et al., (1984) Detection, isolation and continuous production of cytopathic retroviruses (HTLV-III) from patients with AIDS and pre-AIDS. Science 224:497-500). Human immunodeficiency virus (HIV-1) preferentially infects and destroys CD4-positive T-cells. After the discovery of the HIV-1, efforts were directed towards finding drugs which would be effective as anti-HIV agents. Several chemical agents, including interferon, have been tested for their therapeutic potential against HIV-1 (Ho et al., (1985) Recombinant human interferon alpha-A suppresses HTLV-III replication in vitro. Lancet i:602-604; McCormick et al., (1985) Ribavirin suppresses replication of lymphadenopathy associated virus in cultures of human adult T-Lymphocytes. Lancet ii:1367-1369; Mitsuya et al., (1985) 3'-azido-3'-deoxythymidine (BWA509H): an antiviral agent that inhibits the infectivity and cytopathic effect of human-T-lymphotrophic virus type III in vitro. Proc Natl Acad Sci USA 82:7096-7100; Narashima et al., (1986) Inhibition of T-cell lymphotropic virus type III by 3'-azido-3'-deoxythymidine in vitro. Antimicrob Agents Chemother 30:933-937; Anand et al., (1988) Interaction between rifabutin and human immunodeficiency virus type-1; inhibition of replication, cytopathic effect and reverse transcriptase in vitro. Antimicrob Agents Chemother 32:684-688). The dideoxynucleosideanalogue3'-azido-2',3'-dideoxythymidine (AZT) was found to be very efficacious in inhibiting the infectivity and cytopathic effect of HIV-1 in vitro (Mitsuya et al., (1985) 3'-azido-3'-deoxythymidine (BWA509H): an antiviral agent that inhibits the infectivity and cytopathic effect of human-T-lymphotrophic virus type III in vitro. Proc Natl Acad Sci USA 82:7096-7100; Mitsuya et al., (1987) Rapid in vitro systems for assessing activity of agents against HTLV-III/LAV. In AIDS: Modern Concepts and Therapeutic Challenges. Broder, S. (ed.). New York: Marcel Dekker, 303-333). AZT has been shown to increase the survival and decrease the frequency of opportunistic infections in certain patients with AIDS and AIDS-related complex (ARC) (Yarchoan et al., (1988) Phase 1 studies of 3',3'-dideoxycytidine in severe human immunodeficiency virus infection as a single agent and alternating with zidovudine (AZT). Kabcetm 1:76-80). AZT, however, is associated with toxicities that limit its use, particularly bone marrow suppression with megaloblastic changes though the decline in CD4-positive cells has been delayed in patients who have been taking AZT for prolonged periods (Richman et al., (1987) The toxicity of azidothymidine (AZT) in the treatment of patients with AIDS and AIDS-related complex. A double-blind, placebo-controlled trial. New Engl J Med 317:192-197; Yarchoan et al., (1988), supra; Yarchoan et al., (1989) In vivo activity against HIV and favorable toxicity profile of 2',3'-dideoxyinosine. Science 245:412-415). In 1988, AZT-resistant strains of HIV were isolated from patients (Larder et al., (1989) HIV with reduced sensitivity to Zidovudine (AZT) isolated during prolonged therapy. Science 243:1731-1734).

Recently, it was shown that dextran sulphate (DS) has anti-HIV activity and acts synergistically with AZT (Ito et al., (1989) Inhibitory effect of dextran sulfate and heparin on the replication of human immunodeficiency virus in vitro. Antiviral Res 7:361-367; Ueno and Kuno, (1987) Dextran sulfate, a potent anti-HIV agent in vitro having synergism with Zidovudine. (Letter.) Lancet i:1379). Pentosan polysulfate, PPS, like DS, is a negatively charged polysaccharide but has a lower molecular weight (4000 for PPS; >6000 for DS). PPS has been reported to increase the number of circulating T-cells in a subset of migraine patients who have low basophil and T-cell concentration (Thonnard-Neuman and Neckers, (1981) T-lymphocytes in migraine. Ann Allerg 47:325-327; Thonnard-Neuman and Bigelow, (1988) Prophylaxis of migraine with anionic polyelectrolytes. Headache zs:114-120). PPS has also been shown to have low anticoagulant activity (Soria et al., (1980) Anticoagulant activities of a pentosane polysulphate: comparison with standard heparin and function of low molecular weight heparin. Thromb Res 19:455-463; Vinazzer et al., (1980) Influence on the clotting mechanism of sodium pentosan polysulphate (SP-54) in comparison to commercial beef lung sodium heparin. Thromb Res 20:57-68; Baba et al., (1988) Pentosan polysulfate, a sulfated oligosaccharide is a potent and selective anti-HIV agent in vitro. Antiviral Res 9:335-343). In fact, it has been reported that PPS achieves its anti-HIV-1 activity at a concentration 370-fold below its anti-coagulant threshold (Baba et al., (1988), supra. α-cyclodextrin sulphate ("A-CDS") and β-cyclodextrin sulphate ("B-CDS") are cyclical sulphated polysaccharides (Pitha et al., (1988) Drug solubilizers to aid pharmacologists: amorphous cycledextrin derivatives. Life Sci 43:493-502; Pitha, (1989) Pitha, J. (1989) Cyclodextrins: Solutions to Insolubility. Neurotransmissions. V 1-4. Natiok, MA: Research Biochemical Incorporated) whereas PPS is a sulphated polysaccharide with linear configuration (Pentosan Polysulfate (SP-54) Basic Information, published by bene-Arzeneimittel GmbH, Munchen 71, Germany, Mar., 1985). Thus, there is a great need for alternative drugs and combination therapies. The present invention has been accomplished with the above concerns in mind.

SUMMARY OF THE INVENTION

The present invention is directed to an antiviral composition which comprises an antiviral effective amount of an $\alpha$-cyclodextrin sulphate; and a pharmacologically acceptable carrier.

The antiviral composition may also contain an additional other known antiviral agents. In a preferred aspect of the invention, the antiviral composition also includes an antiviral effective amount of AZT.

The antiviral composition according to the present invention may further contain an effective amount of a glucocorticoid.

A further aspect of the invention is directed to a method of treating a viral infection which comprises administering to a patient in need thereof, an antiviral effective amount of an $\alpha$-cyclodextrin sulphate.

The method according to the present invention is useful in treating retroviruses and particularly HIV-1 or HIV-2.

BRIEF DESCRIPTION OF THE DRAWINGS

FIG. 1 is a dose-response relationship of sulphated sugars as tested six days after exposure. Phytohaemagglutinin stimulated human peripheral blood mononuclear cells (PHA-PMNCs) were exposed to A-CDS and PPS and infected with HIV-1 as follows. PMNCs stimulated with 10.0 $\mu$g ml$^{-1}$ of PHA were further propagated in Medium B (RPMI-1640 medium with 10% fetal calf serum, 10% T-cell growth factor, and 1:500 goat antibody to human Interferon) at $10^8$ cells ml$^{-1}$ in 20 ml and were exposed to different concentrations of drugs and simultaneously infected with 10000 c.p.m. ml$^{-1}$ of HIV-1 in 20 ml/culture flask. Cultures were tested for the quantity of cell-free virus in the culture supernatants using the RT method. RT activity in the disrupted virions was tested by using exogenous template poly (rA).(dT)$_{12-18}$ as described (Anand et al., (1988), supra. The reaction mixture consisted of 50mM Tris-hydrochloride (pH 7.5), 5mM dithiothreitol 100mM KCl, 10mM MgClhd 2, 10 $\mu$M [$^3$H]-TTP, Triton X-100 containing poly (rA).(dT)$_{12-18}$ at 30 $\mu$g ml$^{-1}$ (mcg ml$^{-1}$). The reaction mixture was incubated at 37° C. for 2 hours, and [$^3$H]-TTP incorporated into polymers was precipitated with 10% trichloroacetic acid, collected on a glass fibre filter, and counted in an LKB 1219 Rackbeta scintillation counter. Various cultures in the experiment are represented: □-□, A-CDS; o-o, PPS; o-o, B-CDS. The values are means of two determinations tested in two separate experiments. The range of variation was no greater than 15%.

DETAILED DESCRIPTION OF THE PREFERRED EMBODIMENTS

Of the viral infections that can be treated, examples include, but are not limited to, Type C and Type D retroviruses, HTLV-1, HTLV-2, HIV-1, HIV-2, feline leukemia virus, simian immunodeficiency virus, murine leukemia virus, bovine leukemia virus, equine infections, anemia virus, avian sarcoma viruses, such as rous sarcoma virus and the like, hepatitis type A, B, non A/non B, herpes viruses type 1 and 2, cytomegaloviruses, influenza viruses, arboviruses, varicella viruses, measles, mumps and rubella viruses.

MATERIALS AND EXPERIMENTAL PROCEDURES

All percentages herein are by weight unless stated otherwise.

Cell and Viruses

The isolates of HIV-1 used in the studies were LAV-1$_{BRU}$ (Barre-Sinoussi et al., 1983), HIV-1$_{BR}$ (Anand et al., (1989) Biological and molecular characterization of human immunodeficiency virus (HIV-1BR) from the brain of a patient with progressive dementia. Virology 168:79-89 and HIV-1$_{451}$ (Devare et al., (1986) Genomic diversity of the acquired immunodeficiency syndrome retroviruses is reflected in alteration of its translational products. Proc Natl Acad Sci USA 3:5718-5722). These viruses were grown in human PMNCs and the cell-free virus stocks were frozen below $-70°$ C. Human PMNCs were separated from leukophoresed blood with a Flcoll-Hypaque gradient and stimulated by 10 $\mu$g ml$^{-1}$ of phytohaemagglutinin (PHA). After two days, PMNCs were infected and studied for the change in virus replication in the presence of drugs and for the direct effect of drugs on cell multiplication.

Drug Treatment

PMNCs stimulated with PHA were further propagated in Medium B(RPMI-1640 with 10% fetal calf serum. 10% T-cell growth factor and 1:500 diluted goat antibody to human interferon). Virus infection and drug treatments were carried out as required for each experiment (see legends to the figure and tables). In general, four hours after injection and drug treatment, cultures were centrifuged to remove the extracellular virus and the cells were resuspended in fresh Medium B and replenished with appropriate drug concentrations. The percent change in virus replication was calculated as (x-c)/c$\times$100, where x represented the experimental value and c represented the control value.

$\alpha$-cyclodextrin sulfates are readily known and available in the art. $\alpha$-cyclodextrin sulfates can be prepared according to the procedure set forth in U.S. Pat. No. 2,923,704 and U.S. Pat. No. 4,020,160, as well as described in Japan Kokai 75/36,422. $\alpha$-cyclodextrin sulfates can be prepared according to the procedure described herein below.

The A-CDS and B-CDS utilized in the specific examples which follow, which are sulfates of cyclic hexa- and heptamers of glucose, respectively, were prepared according to the following procedure:

Preparation of A-CDS and B-CDS. The procedure is illustrated on the preparation of $\beta$-cyclodextrin sulphate. The procedure is similar to that of Japan Kokai 75 36 422, Chem. Abst. 83:79544a (1975).

To prepare $\beta$-cyclodextrin sulphate, anhydrous pyridine (200 mL) was cooled to $-10°$ C. and while stirring, chlorosulfonic acid (50 mL) was added dropwise so that temperature was kept below 10° C. Afterwards, the flask was heated in an oil bath to 70° C. and anhydrous $\beta$-cyclodextrin (30 g) (manufacturer, Chinoin Pharmaceutical Works, Budapest, Hungary) was slowly added and the mixture kept at 70° C. for another hour. Thereafter, the mixture was, while cooling with ice, decomposed by addition of water (400 mL) and concentrated by evaporation in vaouo. To the concentrate, acetone was added, the precipitate washed with ether, dried and again dissolved in water. The aqueous solution was neutralized with sodium carbonate, dialyzed (48 hr., on shaker), concentrated in vacuo and again precipitated by acetone. The precipitate, after washing and drying, was dissolved in water, clarified and sterilized by filtration through membrane filter (0.45 μm) and freeze-dried to give 33.5 g of β-cyclodextrin sulphate.

α-cyclodextrin sulphate, hydroxypropyl α-cyclodextrin sulphate, and hydroxypropyl β-cyclodextrin sulphate were prepared similarly but omitting the precipitation with acetone, i.e., the reaction mixture, after decomposition with water, was neutralized, dialyzed, and the solution freeze-dried. To make hydroxypropyl α-cyclodextrin sulphate and hydroxypropyl β-cyclodextrin sulphate reagents in 60% and 20% excess, respectively, to those given above were used.

Mass Spectrometry. The instrumentation and conditions used were previously established as optimal for the analysis of heparin fractions according to the procedure of Mallis et al., Anal. Chem. 61' 1453–1458 (1989). Spectra were obtained using a VG ZAB-HF high resolution mass spectrometer equipped with a standard VG analytical fast atom bombardment (FAB) ion source operating in the negative ion mode. Xenon gas was used to form the fast atom; typical conditions were beam energies of 8 keV and a neutral beam current equivalent to 2 mA. The spectra were obtained by signal adding up to eight scans using the multi-channel analysis (MCA) scanning software of the VG 11 250J data system. The samples of cyclodextrin sulfates were dissolved in distilled, deionized water to form a concentration of 10–20 μg/μL. To obtain the spectra, 1 μL of triethanolamine and 2 μL of the solution of cyclodextrin sulphate was placed on a standard VG stainless steel probe tip.

X-Ray Powder Diffraction. A Siemens D-500 automated power diffractometer with graphite monochromator was used. Cu radiation (λ=1.54 Å) was generated from a source operated at 50 kV at 40 mA. Two-theta calibration was performed using NBS mica standard. The samples were kept together in a tightly closed vessel for 100 hrs. at room temperature to equilibrate their water content, and then, just before the measurements, were lightly ground in a mortar.

The method employed for the preparation of sulfates by reaction with chlorosulfonic acid in pyridine was applied to α- and β-cyclodextrin and their hydroxypropyl derivatives. The products thus obtained were all white, water-soluble powders. On the basis of elemental composition, the substitution in α and β-cyclodextrins was not far from two sulphate groups per glucose residue; in sulfates of hydroxypropyl derivatives of α and β-cyclodextrins, which were made using a larger excess of sulfatation reagents, substitutions were higher, 2.6 and close to 3, respectively.

Mass spectra of sulphated carbohydrates are difficult to obtain and no useful results were obtained on cyclodextrin sulfates using $^{252}$Cf plasma desorption spectrometry and fast atom bombardment with glycerol matrix. Fast atom bombardment in the negative ion mode using triethanolamine as a liquid matrix gave well defined mass spectra. The distribution of degree of substitution by sulphate groups was about symmetrical for both sulfates evaluated. The degrees of substitution from 8 to 14 were discernible for α-cyclodextrin sulphate; the most prominent molecular ion was that belonging to degree of substitution 12. In the case of β-cyclodextrin sulphate degrees of substitution from 10 to 17 were observed; the most prominent molecular ion was that belonging to degree of substitution 15.

Powder x-ray diffraction data were measured on preparations of α and β-cyclodextrin sulfates.

The molecular weights of A-CDS and B-CDS are 2400 and 2800, respectively (sodium salt included). PPS(SP-64) and AZT were purchased from Sigma Chemical Co. (St. Louis, MO).

Reverse Transcriptase Assay

Reverse transcriptase activity was tested by using exogenous templates poly (rA).oligo(dT) with the disrupted virions as described in Anand et al., Anti. Microb. Agents Chemother. 32:684–688 (1988). Reduction in RT activity was a reflection of the inhibition of virus production and therefore virus replication. The virus was prepared from the drug-treated and untreated culture supernatants. The reaction mixture was incubated at 37° C. for two hours and [$^3$H]-TTP incorporated into polymers was precipitated with 10% trichloroacetic acid (TCA) collected on glass fibre (Whatman GF-C) and counted in an LKB 1219 Rackbeta scintillation counter as seen in FIG. 1.

Drug Toxicity and Cell Visability

Uninfected PMNCs, drug-treated PMNCs, and drug-treated and virus-infected PMNCs in different experiments were tested for drug toxicity and for the alterations in the numbers of viable cells in response to drug treatment by trypan blue exclusion method.

Inhibitory Effect of Drugs on Virus Replication

The dose-response relationship of the sulphated sugars, A-CDS, PPS and B-CDS, with the replication of HIV-1 was compared in PMNC cultures. Cultures were infected with virus and treated with the drugs simultaneously and were tested to evaluate the amount of virus production by the reverse transcriptase (RT) method. The dose-response relationship showed that A-CDS was more potent than PPS and B-CDS.

Surprisingly, at concentrations of 1.0 μg ml$^{-1}$ or less, however, up to a three-fold increase in virus production was observed in the presence of PPS and B-CDS, but not A-CDS, inhibition of virus replication was further substantiated by using the p24 antigen enzyme-linked immunosorbent assay (ELISA). Intracellular changes in the amount of HIV-1 following exposure to PPS were studied by measuring p24 antigen in the supernatant-free lysed cells. PPS exposure resulted in a decrease in HIV-specific p24 in the cells concomitant with the virus suppression observed in the supernatants using the RT assay and p24 antigen data.

Inhibitory Effect on Reverse Transcriptase Activity

The direct effect of A-CDS, B-CDS and PPS on the reverse transcriptase enzyme activity by treating a detergent-disrupted LAV-1$_{BRU}$ isolate with these drugs and subjecting it to the RT method was examined. PPS inhibited the reaction to 87% at 4.0μg ml$^{-1}$ and over 90% at 5.0μg ml$^{-1}$. The results are reported in Table 1.

TABLE 1

| Direct effect of PPS on RT activity. | | |
|---|---|---|
| Drug conc. (μg ml$^{-1}$) | RT activity (c.p.m. × 10$^3$ ml$^{-1}$) | % >Increase % <Decrease |
| 0.1 | 194 | >7.7 |
| 0.5 | 219 | >21.6 |
| 2.0 | 163 | <9.4 |
| 4.0 | 22 | <87.7 |
| 5.0 | 17 | <90.5 |

TABLE 1-continued

| Direct effect of PPS on RT activity. | | |
|---|---|---|
| Drug conc. ($\mu g\ ml^{-1}$) | RT activity (c.p.m. $\times 10^3\ ml^{-1}$) | % >Increase % <Decrease |
| 6.0 | 17 | <90.5 |
| 8.0 | 9 | <95.0 |
| 10.0 | 7 | <97.7 |
| 15.0 | 4 | <97.7 |
| 20.0 | 2 | <99.8 |
| 25.0 | 1 | <99.4 |
| Control | 180 | 0 |

No inhibition, however, was observed with A-CDS and B-CDS at the concentrations tested (up to $25.0 \mu g\ ml^{-1}$). With PPS, there was an indication of enhancement of the reaction at 0.1 and 0.5 $\mu g\ ml^{-1}$ which suggests that A-CDS and B-CDS do not work by inhibiting RT.

Lymphoproliferative Effect

To understand the mechanism of virus enhancement and to evaluate the toxicity of the sulphated sugars to PMNCs in culture, cell viability counts were performed on trypan blue-stained cells. Sulphated sugars at concentrations up to 100 $\mu g\ ml^{-1}$ were essentially nontoxic to PMNCs, whereas AZT, even at 10nM, showed some toxicity (Table 2). Sulphated sugars in combination experiments were also nontoxic and when used in combination with AZT actually reduced AZT-associated toxicity. The results demonstrated that the sulphated sugars, in addition, exhibited a lymphoproliferative effect since an up to three-fold increase in cell numbers relative to the control cultures was observed, particularly at low drug concentrations. PPS exhibited more lymphoproliferative activity than B-CDS and A-CDS (Table 2). It was further observed that sulphated sugars (PPS more than A-CDS and B-CDS) also had a protective effect on infected cells from HIV-associated cytopathic effect cultures relative to virus-infected drug-free cultures.

TABLE 2

| Lymphoproliferative effect of sulphated sugars on PMNCs. | | | |
|---|---|---|---|
| Drug | Conc. ($\mu g\ ml^{-1}$) | Viable cells $10^4 ml^{-1}$ | % >Increase % <Decrease |
| PPS | 0.1 | 268 | >141 |
| PPS | 0.5 | 202 | <80 |
| B-CDS | 0.1 | 188 | >67 |
| B-CDS | 0.5 | 140 | >25 |
| A-CDS | 0.1 | 140 | >25 |
| A-CDS | 0.5 | 128 | >14 |
| DS | 0.1 | 170 | <51 |
| DS | 0.5 | 90 | >19 |
| AZT(10nM) | — | 72 | <35 |
| Control | — | 118 | 0 |
| Control | — | 106 | 0 |

Anti-HIV synergism Between Sulphated Sugars and AZT

To reduce the required doses of the drugs and to achieve a higher level of anti-HIV activity, we tested possible synergism between the sulphated sugars and AZT. Remarkable synergism was observed between A-CDS and AZT. In the presence of 0.5 and 1.5 $\mu g\ ml^{-1}$ of A-CDS, 10.0nm AZT reduced the virus replication 27.3- and 16.4-fold, respectively, as compared to the 1.2- to 4.9-fold decreases in the presence of either drug individually (Table 3).

TABLE 3

| Synergistic interaction between drugs. | | | |
|---|---|---|---|
| A-CDS ($\mu g\ ml^{-1}$) | AZT (nM) | RT activity (c.p.m. $\times 10^3 ml^{-1}$) | Replication (fold decrease) |
| 0.5 | — | 57 | 2.8 |
| 1.5 | — | 33 | 4.9 |
| — | 10 | 134 | 1.2 |
| 0.5 | 10 | 6 | 27.3 |
| 1.5 | 10 | 10 | 16.4 |
| Control | — | 164 | 0 |

Furthermore, it has been determined that the virus-enhancement effect observed with the low concentration of sulphated sugars was completely abrogated in the combined presence of AZT at 5 and 10nM. Anti-HIV synergism between AZT and B-CDS and AZT and PPS was also observed. When combinations of sulphated sugars (not AZT) were tested for anti-HIV activity, the effect seen was neither synergistic nor antagonistic but was of an additive nature (Table 4).

TABLE 4

| Additive interaction between sulphated sugars. | | | |
|---|---|---|---|
| PPS ($\mu g\ ml^{-1}$) | B-CDS ($\mu g\ ml^{-1}$) | RT activity (c.p.m. $\times 10^3 ml^{-1}$) | Replication <% decrease |
| 2.0 | — | 43 | 77.0 |
| — | 2.5 | 112 | 40.1 |
| 2.0 | 2.5 | 18 | 90.3 |
| Control | — | 187 | 0 |

A-CDS, PPS and B-CDS were found to be potent inhibitors of HIV-1 replication in PMNC cultures. PPS, like DS, has been reported to block the adsorption of HIV-1 on the cells and inhibit RT activity in vitro (Baba et al., (1988), supra; Bagasara and Lischner, (1988) Activity of dextran sulfate and other polyanionic polysaccharides against human immunodeficiency virus. J Inf Dis 158:1084–1087; Mitsuya et al., (1988) Dextran sulfate suppression of viruses in the HIV family: inhibition of viron binding to CD4 cells. Science 240:646–649).

The lymphoproliferative activity of A-CDS, B-CDS and PPS on PMNCs in culture is potentially extremely important in view of the immunosuppression in AIDS patients. Similarly, the protective effect of these drugs on PMNCs from HIV-associated cell death observed in our experiments would be helpful in controlling immunosuppression. The anti-HIV and lymphoproliferative activities present in the same chemical compounds have obvious benefits for the control of AIDS.

A transient increase in virus replication observed with PPS and B-CDS (but not with A-CDS) at lower drug concentrations could be due to a combination of factors. However, it is encouraging that the virus enhancement effect of sulphated sugars was completely abrogated in the presence of very low amounts (5-10nM) of AZT.

The synergistic interaction between A-CDS and AZT is particularly important. For example, in the presence of 0.5 $\mu g\ ml^{-1}$ of A-CDS, AZT at 10nM resulted in about a 25-fold decrease in HIV replication in PMNCs relative to the situation when the drugs were used alone. In clinical trials with AZT, an effort is usually made to achieve $3\mu M$ serum levels which apparently result in toxic doses of AZT (Mitsuya et al., (1987) Rapid in vitro systems for assessing activity of agents against HTLV-III/LAV. In AIDS: Modern Concepts and Therapeutic Challenges. Broder, S. (ed.). New York: Marcel Dekker, 303–333; Richman et al., (1987), supra. The marked synergism observed between AZT and sulphated sugars may allow the use of AZT at considerably lower concentrations in vivo in combination with A-CDS or PPS, which possess the additional advantage of having lymphoproliferative activity. In addition, different combinations of sulphated sugars (in the absence of AZT) resulted in additive anti-HIV activity and effects of individual drugs were maintained, suggesting that multiple drug combinations may be achievable. A-CDS, B-CDS and PPS (up to 100 μg ml$^{-1}$) were nontoxic to PMNCs in culture. A-CDS is more potent in anti-HIV action than PPS, B-CDS and DS and unexpectedly apparently lacks the virus-enhancement effect seen with PPS, B-CDS and DS. Because of the anti-HIV activity, lymphoproliferative effect, additive effect of A-CDS with PPS and profound synergistic effect of A-CDS with AZT, and their apparent lack of toxicity (in vivo and in vitro), A-CDS could be developed along with AZT into an extremely potent combination chemotherapy for AIDS. Such combination chemotherapy could have dual action which would allow potent anti-HIV activity at lower doses of AZT (lower than shown to be toxic in vivo) and could also help build the immune system as a result of the lymphoproliferative nature of these sulphated sugars.

Anti-HIV Effects of Sulphated Sugars in Presence of Glucocorticoids. HIV infections are at some later stages invariably complicated by pathologies which involve neovascularization, particularly those associated with Kaposi's sarcoma. Previously, Folkman et al., *Science* 243, 1490–1493, 1989, observed that B-CDS stimulates this particular pathology, but that this side-effect can be suppressed by glucocorticoids. Results in Table 5, obtained by the same techniques as those in previous examples, show that glucocorticoids do not suppress antiviral effects of A-CDS. Thus, pathological neovascularization can be avoided without comprising the anti-HIV effects.

TABLE 5

Effects of Hydrocortisol Phosphate and α-Cyclodextrin Sulfate on Cell Prolification and HIV-1 Replication

| Concentration of α-cyclodextrin sulfate (μg/ml) | Concentration of hydrocortisone phosphate (μg/ml) | Inhibition of HIV-1 reverse transcriptase activity (%)* | Cell Count in million per mL |
|---|---|---|---|
| — | 5 | 39 | 1.2 |
| — | 5 | 20 | 1.0 |
| 0.5 | — | 77 | 2.0 |
| 1.0 | — | 72 | 1.0 |
| 2.5 | — | 80 | 1.2 |
| 5.0 | — | 83 | 1.3 |
| 10.0 | — | 91 | 1.5 |
| 0.5 | 5 | 84 | 1.3 |
| 1.0 | 5 | 84 | .8 |
| 2.5 | 5 | 82 | 1.1 |
| 5.0 | 5 | 88 | 1.3 |
| 10.0 | 5 | 94 | 1.0 |

*100% value (viral infection, no drug) 2775 and 2308 cpm
0% value (no infection, no drug) 33 and 39 cpm Pharmaceutical Compositions The α-cyclodextrin sulfates may be made into pharmaceutical compositions by combination with appropriate, pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration.

The α-cyclodextrin sulfates can be used, singularly alone, in combination with each other, or in combination with other antiviral agents. When patients infected with HIV-1 and/or HIV-2 are being treated, α-cyclodextrin sulfates can be co-administered with AZT.

The α-cyclodextrin sulfates can also be co-administered with glucocorticoids.

The following methods and excipients are merely exemplary and are in no way limiting.

In pharmaceutical dosage forms, the α-cyclodextrin sulfates may be used in the form of their pharmaceutically acceptable salts, and also may be used alone or in appropriate association, as well as in combination with other pharmaceutically active compounds, e.g., other known antiviral agents.

In the case of oral preparations, the α-cyclodextrin sulfates may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The α-cyclodextrin sulfates preferably may be formulated into preparations for injections by dissolving or suspending them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The injectable preparations can be administered intravenously, intramuscularly, intraperitoneally, and the like.

The α-cyclodextrin sulfates can be utilized in aerosol formulation to be administered via inhalation. The α-cyclodextrin sulfates can be formulated into pressurized acceptable propellants such as dichlorodifluoromethane, propane, nitrogen and the like.

Furthermore, the α-cyclodextrin sulfates may be made into suppositories by mixing with a variety of bases such as emulsifying bases or water-soluble bases. The α-cyclodextrin sulfates can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, e.g., teaspoonful, tablespoonful, tablet or suppository contains a predetermined amount of the composition containing α-cyclodextrin sulfates similarly, unit dosage forms for injection or intravenous administration may comprise a michellamine composition as a solution in sterile water, normal saline or other pharmaceutically acceptably carrier.

The term "unit dosage form" as used herein refers to physically discrete units suitable as unitary dosages for human and animal subjects, each unit containing a predetermined quantity of α-cyclodextrin sulfates calculated in an amount sufficient to produce the desired effect in association with a pharmaceutically acceptable, diluent, carrier or vehicle. The specifications for the novel unit dosage forms of the present invention depend on the particular α-cyclodextrin employed and the effect to be achieved, and the pharmacodynamics associated with each compound in the host.

The pharmaceutically acceptable excipients, for example vehicles, adjuvants, carriers or diluents, are readily available to the public.

One skilled in the art can determine easily the appropriate method of administration for the exact formulation of the composition being used. Any necessary adjustments in dose can be made readily to meet the nature or severity of the infection and adjusted accordingly by the skilled practitioner.

Use of Compositions Containing α-cyclodextrin Sulfates for Treating Viral Infections The present invention relates further to a method of treating viral infections comprising the administration of an antiviral effective amount of the composition of the present invention. Antiviral effective amount is defined as that amount of compound required to be administered to an individual patient to achieve an antiviral effective blood and/or tissue level to inhibit the virus. The antiviral effective blood level might be chosen, for example, to inhibit a virus in a screening assay. An example of such an amount would be 20–200 μM. Alternatively, the antiviral effective blood level can also be defined as that concentration which inhibits markers (e.g., p24) of the virus in the patient's blood, or which renders the patient asymptomatic to the particular viral infection. Since a fixed antiviral effective blood level is used as the preferred endpoint for dosing, the actual dose and schedule for drug administration for each patient will vary depending upon interindividual differences in pharmacokinetics, drug disposition and metabolism. Moreover, the dose may vary when the compounds are used prophylactically or when used in combination with other drugs.

Such dosage amounts can be readily ascertained without undue burden and experimentation by those skilled in the art.

As an example of an antiviral effective amount, the parenteral dosage for humans can range from about between 0.01 mg/kg body weight to 1200 mg/kg body weight.

While the foregoing invention has been described in some detail for purposes of clarity and understanding, it will be appreciated by one skilled in the art from a reading of this disclosure that various changes in form and detail can be made without departing from the true scope of the invention.

We claim:

1. An antiviral composition which comprises an antiviral effective amount of an α-cyclodextrin sulphate, an antiviral effective amount of an additional antiviral agent; and a pharmaceutically acceptable carrier.

2. The antiviral composition according to claim 1 wherein said additional antiviral agent is AZT.

3. An antiviral composition which comprises an antiviral effective amount of an α-cyclodextrin sulphate, an effective amount of a glucocorticoid; and a pharmaceutically acceptable carrier.

4. The antiviral composition according to claim 3 wherein the glucocorticoid is hydrocortisone.

5. The antiviral composition according to claim 4 additionally containing an antiviral effective amount of an additional antiviral agent.

6. The antiviral composition according to claim 5 wherein said antiviral gent is AZT.

7. The antiviral composition according to claim 3 which additionally contains an antiviral effective amount of AZT.

8. The antiviral composition according to claim 3 which additionally contains an antiviral effective amount of an antiviral agent.

9. A method of treating a viral infection which comprises administering to a patient in need thereof, an antiviral effective amount of a composition comprising an antiviral effective amount of an α-cyclodextrin sulphate and pharmaceutically acceptable carrier.

10. The method according to claim 9, wherein said viral infection is caused by a retrovirus.

11. The method according to claim 10, wherein said retrovirus is HIV-1 or HIV-2.

12. The method according to claim 9, further comprising administering an antiviral effective amount of AZT.

13. The method according to claim 9, further comprising administering an effective amount of a glucocorticoil.

* * * * *